United States Patent [19]
Osawa et al.

[11] Patent Number: 5,993,795
[45] Date of Patent: Nov. 30, 1999

[54] PROTEIN COMPOSITION DERIVED FROM SESAME SEED AND USE THEREOF

[75] Inventors: Toshihiko Osawa, Aichi; Keiko Nagai, Osaka; Kyoko Shibuya, Nara, all of Japan

[73] Assignee: Takemoto Yushi Kabushiki Kaisha, Gamagori, Japan

[21] Appl. No.: 08/745,126

[22] Filed: Nov. 8, 1996

[30] Foreign Application Priority Data

Nov. 9, 1995 [JP] Japan ...................................... 7-291177

[51] Int. Cl.$^6$ .............................. A61K 7/06; C11D 3/382
[52] U.S. Cl. ......................... 424/74; 424/401; 514/846; 514/845; 514/844; 514/881; 510/119
[58] Field of Search ............................... 426/44; 530/370, 530/377, 378; 514/844, 845, 846, 881; 510/119; D28/4; 424/401, 74

[56] References Cited

U.S. PATENT DOCUMENTS

| | | | |
|---|---|---|---|
| 3,966,971 | 6/1976 | Morehouse et al. | 426/444 |
| 4,088,795 | 5/1978 | Goodnight et al. | 426/598 |
| 4,370,267 | 1/1983 | Lehnhardt et al. | 260/123.5 |
| 4,438,095 | 3/1984 | Grollier et al. | 424/78 |
| 4,810,498 | 3/1989 | DiMeglio | 424/195.1 |
| 5,086,166 | 2/1992 | Lawhorn et al. | 530/378 |
| 5,180,588 | 1/1993 | Shinmen et al. | 424/439 |

FOREIGN PATENT DOCUMENTS

| | | |
|---|---|---|
| 2 705 031 | 11/1994 | France . |
| 1-206956 | 8/1989 | Japan . |
| 4-149138 | 5/1992 | Japan . |

OTHER PUBLICATIONS

Perez et al. Archivos Latinoamericanos de Nutricion 34(4): 735–748, 1984.
Sreekantiah et al. Food Technol. (Chicago) 23(8): 1055–1061, 1969.
Saad et al. Archivos Latinamericanos de Nurtricion 34(4): 749–762, 1984.
Yu et al. Food & Fermentation Industries No. 2: 8–13, 1994.
M.J. Guerra et al., "Extraction of Sesame Seed Protein and Determination of its Molecular Weight by Sodium Dodecyl Sulfate Polyacrylamide Gel Electrophoresis", J. of the Amer. Oil Chemists' Society, vol. 52:73–75 (1975).
Kuriyama and Murui, "Scavenging of Hydroxy Radicals by Ligna Glucosides in Germinated Sesame Seed", Nippon Nogeikagaku Kaishi, 69(6):703–705 (1995).

*Primary Examiner*—Chris Eisenschenk
*Assistant Examiner*—Mary K Zeman
*Attorney, Agent, or Firm*—Finnegan, Henderson, Farabow, Garrett & Dunner, L.L.P.

[57] ABSTRACT

A protein composition derived from sesame seed is disclosed, which contains 40–95% by weight of crude proteins, 1–50% by weight of carbohydrate, 0–5% by weight of fat, 0–1% by weight of fiber, and 0.2–3% by weight of physiologically active substances derived from sesame seed, based on the dry weight of the composition and which is characterized in that when the protein composition is suspended at room temperature in pure water of pH 7 at a concentration of 5% by weight, not less than 80% by weight of the protein composition is dissolved in the pure water. A foodstuff or a cosmetic article containing the protein composition is also disclosed.

4 Claims, No Drawings

PROTEIN COMPOSITION DERIVED FROM SESAME SEED AND USE THEREOF

BACKGROUND OF THE INVENTION

1. Field of the Invention

The present invention relates to a protein composition derived from sesame seed which excels in solubility in water and digestive assimilability, enjoys great practical utility as material for foodstuffs, and fits safe application as material for cosmetic articles and to foodstuffs using the composition.

2. Description of Prior Art

It has been known for long that sesame seed is an excellent food from the nutritional point of view. The sesame seed is used wholly as food in various forms such as roast sesame, ground sesame, roasted dehulled sesame, and pasted sesame. It is otherwise used widely in the form of sesame oil obtained by squeezing or by extraction with solvent.

Though the defatted oil cake which remains after the removal of sesame oil from sesame seed by squeezing or by extraction with solvent has high contents of proteins, carbohydrate, and physiologically active substances all abounding in nutritive value, it finds very little utility for practical applications except feed for domestic animals and fertilizer.

Though the defatted oil cake after the defatting predominantly comprises proteins of high quality, it manifests virtually no solubility in water. The scanty solubility imposes a strict limit on the kinds of applications to be found for the oil cake and the manners of application because it prevents the oil cake from being easily handled while it is being incorporated into foodstuffs and cosmetic articles.

As a means to obtain proteins from sesame seed, the method which collects proteins from oil cake which was roasted and then compressed by subjecting the oil cake to a heat treatment by the use of an acidic aqueous solution (Japanese Unexamined Patent Publication No. 01-206956) may be cited. Since this method collects the proteins from thermally degenerated defatted oil cake by adjusting the oil cake to a pH value of not more than 2, keeping it at or above 70° C. thereby extracting proteins, causing the extracted proteins to precipitate in a neutral zone, and isolating the precipitate, the collected proteins exhibit solubility in water exclusively in an acidic zone and defies solution in neutral water. Further, since the collected proteins themselves are obtained in an undecomposed state, they are at a disadvantage in having a large molecular weight and manifesting no satisfactory digestive assimilability.

For the purpose of decreasing the molecular weight, the method for hydrolyzing the proteins by the use of an enzyme may be conceived. The method disclosed in Japanese Unexamined Patent Publication No. 04-149138 represents a case of hydrolyzing the proteins by simultaneous use of a plurality of enzymes. This method implements the hydrolysis of proteins of soybeans, for example, by simultaneous addition of three kinds of enzymes to the proteins. The product of this hydrolysis principally comprises peptides which have notably low molecular weights averaging in the approximate range of 290–350. It is aimed at fulfilling the function of attaining recovery from fatigue and does not contain physiologically active substances derived from sesame seed. The invention covering this method suggests absolutely nothing about the use of sesame seed as the raw material.

A composition which contains proteins derived from sesame seed, also contains peculiar physiologically active substances derived from sesame seed, and has the proteins principally comprising crude proteins partially converted into peptides and possessing molecular weights distributed in a wide range is expected to excel in solubility in water and digestive assimilability and find extensive utility in applications such as foodstuffs and cosmetic articles. This ideal composition remains yet to be developed.

The subject imposed on the present invention consists in providing a protein composition derived from sesame seed which makes effective use of heretofore unused proteins of sesame seed, contains proteins exhibiting solubility in water unlike the ordinary water-insoluble defatted oil cake, as the proteins principally comprise crude proteins partially converted into peptides and possessing molecular weights distributed in a wide range, and further contains antioxidant precursors such as lignan glycosides and physiologically active substances peculiar to sesame seed such as antioxidant lignans.

SUMMARY OF THE INVENTION

After continuing a diligent study with a view to fulfilling the subject mentioned above, the present inventors have found that by using as a main component crude proteins partially converted into peptides and possessing molecular weights distributed in a wide range and, at the same time, making effective use of the heretofore unused proteins of sesame seed, a protein composition which excels in solubility in water and digestive assimilability, contains antioxidant precursors such as lignan glycosides and physiologically active substances peculiar to sesame seed such as antioxidant lignans, and enjoys high nutritive value is obtained.

To be specific, the present invention concerns a protein composition derived from sesame seed, containing 40–95% by weight of crude proteins, 1–50% by weight of carbohydrate, 0–5% by weight of fat, 0–1% by weight of fiber, and 0.2–3% by weight of physiologically active substances derived from sesame seed, based on the dry weight of the composition and characterized in that when the protein composition is suspended at room temperature in pure water of pH 7 at a concentration of 5% by weight, not less than 80% by weight of the protein composition is dissolved in the pure water.

The present invention further concerns a protein composition derived from sesame seed which is obtained by treating defatted oil cake with an enzyme.

The present invention further concerns a protein composition derived from sesame seed which is obtained from defatted oil cake by using n-hexane.

The present invention further concerns a protein composition derived from sesame seed, wherein components having molecular weights not less than 50,000 are contained at a concentration in the range of 0–40% by weight and components having molecular weights not more than 5,000 at a concentration in the range of 5–60% by weight.

The present invention further concerns a protein composition derived from sesame seed, wherein the amino acid composition of the crude proteins has a content of sulfur containing amino acids in the range of 4–6%.

The present invention further concerns a method for the production of the protein composition derived from sesame seed, characterized by treating sesame seed or defatted oil cake with an enzyme.

The present invention further concerns a method for the production of the protein composition derived from sesame seed, characterized by extracting protein from sesame seed or defatted oil cake and treating the resultant protein extract with an enzyme.

The present invention further concerns a foodstuff or a cosmetic article containing the protein composition derived from sesame seed.

The present invention further concerns a method for supply of nutrition, characterized by the ingestion of the protein composition derived from sesame seed or the foodstuff.

The present invention further concerns a cosmetic article containing the protein composition derived from sesame seed.

The present invention further concerns a method for supply of nutrition, characterized by the using the cosmetic article.

DETAILED DESCRIPTION OF THE INVENTION

The present invention will be described in detail below.

In the present invention, the content of the crude proteins is expressed by the total amount of proteins, peptides, and amino acids. And the content of the physiologically active substances derived from sesame seed is expressed the total amount of sesaminol glycosides, sesamin and sesamolin.

The sesame seed to be used as the raw material for the protein composition of the present invention may be any of various known forms such as, for example, raw sesame seed, dehulled raw sesame seed, and roast sesame seed. As respects the species, white sesame, black sesame, golden sesame, and brown sesame seed are invariably usable as the raw material. Concerning the geographic origin, tropical sesame, subtropical sesame, and temperate sesame seed are invariably usable appropriately.

The method for the preparation of the protein composition of the present invention is only required to be capable of obtaining a composition fulfilling the essential qualities. Though the protein composition may be prepared by directly extracting proteins from sesame seed, it is appropriate to use as the raw material such sesame seed as has been defatted in advance. The defatting is effected by any of the known methods such as, for example, extraction using organic solvent or squeezing. The defatting treatment performed on raw sesame seed by the use of organic solvent proves particularly advantageous because it can be implemented without requiring any heat treatment at elevated temperatures. As concrete examples of the organic solvent which is used appropriately for the defatting treatment, n-hexane, ethanol, and ethyl acetate may be cited. Among other organic solvents mentioned above, n-hexane is used particularly advantageously. It goes without saying that the fat which result from the defatting treatment can be effectively utilized as sesame oil.

In consideration of the efficiency of defatting, it is advantageous for the sesame seed to be ground before it is subjected to the defatting treatment with the organic solvent. The grounding of sesame seed may be effected by any of the known methods such as, for example, the method of flattening the individual seed particles by the use of a rolling mill and the method of cutting the individual seed particles by the use of a mill.

When the sesame seed is dehulled before it is used for the preparation of the protein composition, the ultimately produced protein composition enjoys increased whiteness and decreased odor and, therefore, prove advantageous for the purpose of addition to foodstuffs and cosmetic articles. The hulling of sesame seed may be attained by suitably using any of the known methods such as, for example, the method which effects the removal of hulls by mechanical friction and the method which attains the removal of hulls by dissolving the hulls with an alkaline aqueous solution.

When the protein composition contains crude proteins of relatively low molecular weights of not more than 5,000 in a large amount, it enjoys heightened solubility in water and improved digestive assimilability as food. For this reason, it is appropriate for the protein composition of the present invention to contain components having molecular weights of not more than 5,000 at a concentration in the range of 5–60% by weight, preferably 10–60% by weight, and more preferably 20–60% by weight. When the protein composition contains crude proteins of relatively large molecular weights of not less than 50,000 in a large amount, it suffers decreased solubility in water and degraded digestive assimilability as food. It is appropriate, therefore, for the protein composition to contain components having molecular weights of not less than 50,000 at a concentration in the range of 0–40% by weight, preferably 0–30% by weight.

For the purpose of obtaining with high efficiency the protein composition containing crude proteins of molecular weights of not more than 5,000 in a large amount and crude proteins of molecular weights of not less than 50,000 in a small amount, it is appropriate to hydrolyze the proteins in the sesame seed. Though the hydrolysis of the proteins may be carried out directly on sesame seed or defatted oil cake, it may be effected on the protein extract obtained by extracting the proteins in a dissolved state from the sesame seed.

Though the method for extracting the proteins in the dissolved state from the sesame seed is not particularly limited, the extraction by the use of an alkali or a salt can be carried out advantageously. As concrete examples of the alkali which is appropriately used for the extraction of proteins, NaOH, KOH, and alkali metal phosphates such as $K_3PO_4$ and $Na_3PO_4$ may be cited. As concrete examples of the salt which is effectively used for the extraction of proteins, NaCl and KCl may be cited. This extraction of proteins in the dissolved state is appropriately carried out with the pH value adjusted in the range of 8–12 at a temperature in the range of 40–100° C. for a period in the range of 10–120 minutes. The amount of the enzyme or the acid to be used as will be described specifically hereinafter can be decreased by subjecting the extract resulting from the extraction of proteins in the dissolved state to a hydrolyzing treatment.

For the purpose of hydrolyzing the proteins of sesame seed, it is appropriate to utilize the action of an enzyme capable of hydrolyzing proteins. The enzyme which is properly used for this purpose is any of the enzymes belonging to the class proteases and the class peptidases which originate in fungi and microbes, animals, and plants.

The enzyme may be a product of the user's own development or a commercially available product. The use of two or more, particularly three or more, kinds of enzymes in the reaction is advantageous because the water-soluble composition can be obtained with a high yield and the content of crude proteins having molecular weights of not more than 5,000 can be increased.

As concrete examples of the commercially available proteases, Protease S, Protease N, Protease P, and Pancreatin F produced by Amano Pharmaceutical Co., Ltd. and Alkalase produced by Novo Nordics may be cited. These commercially available proteases may be used in the form of a combination of two or more members. The combination of Protease N, Protease S, and Pancreafin F is a typical example of the various conceivable combinations of the enzymes.

The treatment with two or more kinds of enzymes can be carried out by using the plurality of kinds of enzymes all at once or sequentially. The plurality of kinds of enzymes may be added simultaneously to the reaction system or they may be mixed and the resultant mixture may be added to the reaction system. When the two or more enzymatic reactions are carried out simultaneously, the operation is accomplished efficiently in terms of the time spent for the reactions and the convenience of work.

For the purpose of enabling the enzymatic treatment of sesame seed or defatted oil cake to proceed efficiently, the sesame seed or the defatted oil cake is preferably ground prior to the treatment. In the case of the defatted oil cake, the grounding may be performed either prior to the defatting or after the defatting and prior to the enzymatic treatment. When the defatting is effected with organic solvent, it is preferable for the sake of the efficiency of defatting to perform the grounding prior to the defatting.

The sesame seed which has been defatted by squeezing contains more fat than the sesame seed which has been defatted with organic solvent. When the sesame seed which has been defatted by squeezing is used in its unmodified form, the produced composition is liable to contain fat in a large amount. For the purpose of obtaining the composition having a small fat content, therefore, it is appropriate that the sesame seed defatted by squeezing is further deprived of the fat by the use of an organic solvent capable of dissolving the fat and then subjected to the enzymatic treatment. The sesame seed which has been defatted by squeezing may be directly used to produce a composition having a large fat content and then deprived of the fat by the use of the organic solvent mentioned above.

For the sesame seed which has been defatted by squeezing, the organic solvent which dissolves fat as described above is properly used. For the purpose of obtaining a protein composition containing water-soluble physiologically active substances in a large amount, it is proper to use such an organic solvent as dissolves fat and avoids dissolving water-soluble physiologically active substances. Such organic solvents as n-hexane and ethyl acetate, therefore, are used more advantageously than such organic solvents as ethanol and methanol which dissolve water-soluble physiologically active substances.

The amount of an enzyme, the reaction time, and the reaction conditions in the enzymatic treatment can be suitably selected depending on the characteristics of the enzyme to be used. Appropriately, the amount of the enzyme to be added is in the range of 0.5–6%, preferably 1–4%, based on the amount of the substrate, the amount of the substrate is in the range of 1–20%, preferably 5–16%, based on the amount of a solvent, the pH value is in the range of 3–12, preferably 4.5–10.5, the reaction temperature is in the range of 35–75° C., preferably 45–55° C., and the reaction time is in the range of 2–12 hours, preferably 3–6 hours. The solvent to be used is suitably selected on the condition that it possesses a pH value in the range specified above and avoids impeding the enzymatic reaction. As concrete examples of the solvent which is advantageously used herein, water, carbonate buffer, and phosphate buffer may be cited. The solvent, when necessary, may have the pH value thereof adjusted with an acid or a base.

Appropriately, the enzyme is inactivated by a suitable means such as a heat treatment after completing the reaction.

The product of the enzymatic treatment consequently obtained is separated by a suitable means such as centrifugal separation or filtration into an insoluble fraction and a soluble fraction. Depending on the final use for which the produced composition is intended, a soluble fraction in a specific pH range is separated. When the fraction is expected to be soluble in a neutral range, for example, it can be separated by preparing the product of the enzymatic treatment in a neutral form and then removing the insoluble fraction therefrom.

The soluble fraction which remains after the removal of the insoluble fraction may be either used in its unmodified form as a protein composition or dried and then used as a powdered composition. The drying may be suitably effected by any of popular methods such as freeze drying and spray drying.

The hydrolysis of proteins of sesame seed by the use of enzyme has been described by citing examples. The present invention does not limit the hydrolysis to this form. The hydrolysis can be effected in the presence of an acid. This acid may be any of such strong acids as hydrochloric acid and sulfuric acid. The acid concentration is appropriately in the range of 0.05–3 N, preferably 0.1–2 N. If the acid concentration exceeds 3 N, the amount of physiologically active substances contained in the protein composition will possibly decrease. The molecular weights of proteins can be controlled by adjusting the acid concentration, treating temperature, treating time and so on. After the hydrolysis with an acid, the hydrolyzate is neutralized to a specific pH value with a suitable alkali and then separated by centrifugation or filtration to expel an insoluble fraction and obtain a soluble fraction.

The protein composition derived from sesame seed which is obtained as described above contains 40–95% by weight, preferably 50–95% by weight, of crude proteins (proteins, peptides, and amino acids), 1–50% by weight, preferably 5–40% by weight, of carbohydrate, 0–5% by weight, preferably 0–3% by weight, of fat, 0–1% by weight, preferably 0–0.5% by weight, of fiber, and 0.2–3% by weight, preferably 0.4–3% by weight, of physiologically active substances (sesaminol glycosides, sesamin, and sesamolin) derived from sesame seed, based on the dry weight of the composition. When this protein composition derived from sesame seed is suspended at room temperature in pure water of pH 7 at a concentration of 5% by weight, not less than 80% by weight of the protein composition is dissolved in the pure water.

The amino acid composition of the crude proteins as the main component of the protein composition of the present invention is characterized by having a high content of sulfur containing amino acids as compared with the amino acid composition of soybean protein. While the content of sulfur containing amino acids in the amino acid composition of soybean protein is generally in the approximate 2.1% and that of peanut is about 2.0%, the content of sulfur containing amino acids in the crude proteins of the protein composition of the present invention is not less than 3.5%, preferably in the range of 4–6%. This magnitude is close to that of such animal protein as is represented by 3.5% for beef, 5.5% for egg or 4.0% for turkey. This fact indicates that the protein composition of the present invention particularly fits addition to foodstuffs and animal feed. When the protein composition of the present invention and the soybean protein are simultaneously used, they manifest an effect of complementing each other in exalting the nutritive value of protein. Further, since the protein composition of the present invention has a low fat content as evinced by the fact that the fat content is not more than 5% by weight, it can be favorably used as a functional food for dieters.

The lignan glycosides, water-soluble physiologically active substances contained peculiarly in sesame seed, are antioxidant precursors. The lignan compounds have antioxidative activities. The protein composition of the present invention which contains the crude proteins and the lignan glycosides, therefore, can be used effectively in various applications.

The protein composition of the present invention accordingly can be advantageously used not only as the raw material for foodstuffs but also as the raw material for cosmetic articles. This protein composition, when necessary, can have even the color tone, flavor, and smell thereof regulated by selecting the production conditions.

Since the protein composition of the present invention is soluble in water, it can be used equally in foodstuffs and in other articles without reference to choice between powder and solution in terms of form of application. Thus, it finds extensive utility. Since the proteins as the main component of this composition contain crude proteins of relatively small molecular weights of not more than 5,000 in a large amount, the protein composition of the present invention is at an advantage in manifesting high solubility in water and enjoying ideal digestive assimilability for food.

Further, the protein composition of the present invention manifests solubility in alcohols. In an aqueous 10% ethanol solution, for example, about 5% by weight of the protein composition is almost thoroughly dissolved. Thus, the protein composition of the present invention can be favorably used in alcoholic beverages and can be appropriately used as the raw material for cosmetic articles.

The foodstuffs containing the protein composition of the present invention can be utilized in various applications as highly satisfactory nutritive supplements. This protein composition can be added in an amount in the range of 0.1–50% by weight to foodstuffs. Particularly when it is added in an amount in the range of 1–5% by weight to food, it can impart a fine flavor to the food. Since the protein composition is soluble in water, it can be easily added to drinks and other liquids. For addition to foodstuffs of solid and other states, it can be used in the form of a solution and added uniformly. Since, the protein composition excels in digestive assimilability, it can be added in the form of powder to foodstuffs.

The protein composition of the present invention can be used very satisfactorily in any of various forms of foodstuffs such as, for example, solid foodstuffs including cookies and breads, liquid foodstuffs including soup, drinks to relieve fatigue, juice, and lactic acid beverage, and gel or creamy foodstuffs including pudding, jelly, and yogurt.

Further, the protein composition of the present invention can be mixed with such cosmetic articles as shampoo, cosmetic lotion, and cosmetic cream. These cosmetic articles have no smell of animal protein and have good effect of moisturizing and protecting. The amount of the protein composition to be added to such cosmetic articles is appropriately in the approximate range of 0.1–5% by weight, though variable with the kinds of cosmetic articles.

Besides, the protein composition of the present invention can be incorporated in feed for domestic animals and consequently enabled to give rise to functional animal feed of high nutritive value. The amount of the protein composition to be added to the feed is appropriate in the approximate range of 0.1–50% by weight, preferably 1–5% by weight.

The present invention will be described more specifically below with reference to examples. It should be noted, however, that the scope of the present invention is not limited to these examples.

The solubility and molecular weight of a protein composition, and the contents of crude proteins, carbohydrate, fat, fibers, and physiologically active substances in a given range of molecular weight which are mentioned in the examples were determined as follows.

Method for determination of solubility: The solubility of a sample protein composition was determined by suspending the sample in pure water of pH 7 at room temperature (25° C.) at a concentration of 5% by weight, measuring the soluble fraction in % by weight, and reporting the results of the measurement.

Method for analyzing molecular-weight distribution: This analysis was effected by passing a sample before freeze drying through a filter of a mesh size of 0.22 μm and subjecting the filtrate to HPLC under the following conditions. The molecular weight was determined by preparing a calibration curve by the use of molecular weight markers and comparing the found values with the values on the calibration curve.

(Conditions for HPLC analysis)
Column used: Develosil 300-Diol (produced by Nomura Chemical Co., Ltd.)
Column diameter: 8 mm
Column length: 300 mm
Mobile phase: 0.1M phosphate buffer (pH 6.8) containing 0.2M NaCl
Flow rate: 0.5 ml/min
Detection: 215 nm
Temperature of measurement: 37° C.
Amount of sample: 15 μl Crude protein content: This amount was determined by the Kjeldahl method (protein coefficient: 6.25).

Content of sulfur containing amino acids: This amount was determined by the amino acid auto analysis method.

Fat content: This amount was determined by the Soxhlet extraction method.

Fiber content: This amount was determined by the improved Henneberg-Stohmann method.

Carbohydrate content: This amount was determined by the calculation of the following formula.

{1-(Water content+protein content+fat content+fiber content+ash content)}×100 (%)

Physiologically active substances (sesaminol glycosides, sesamine, and sesamolin) content: These amounts were determined by measuring the total amounts of sesaminol glycosides, sesamine, and sesamolin.

Specifically, this determination was performed by dispersing a given sample in ten times its weight of 80% ethanol, shaking the dispersion at room temperature for 18 hours, centrifuging the resultant solution to expel an insoluble fraction, passing the soluble fraction through a filter of a mesh size of 0.22 μm and obtaining a specimen for analysis, and subjecting this specimen to HPLC under the following conditions to analyze physiologically active substances. For the identification and determination of peaks, the standard substances for relevant physiologically active substances were used.

(Conditions for HPLC analysis)
Column used: Develosil ODS-5 (produced by Nomura Chemical Co., Ltd,)
Column diameter: 6 mm
Column length: 250 mm
Mobile phase: [Linear gradient of methanol: water]
  MeOH concentration 30%→80% in 40 minutes
  MeOH concentration 100% in 5 minutes
  MeOH concentration 100%→30% in 2 minutes
  MeOH concentration 30% in 13 minutes
Flow speed: 1.0 ml/min
Detection: 290 nm
Sample size: 30 μl

EXAMPLE 1

Brown sesame seed imported from Guatemala was adopted as a raw material, dehulled with an alkaline aqueous solution, then ground by the use of a mill, and defatted with n-hexane to obtain 200 g of defatted oil cake. In 1.6 liters of a 50 mM carbonate buffer (pH 9.0), 200 g of the defatted oil cake was suspended. The resultant suspension and 4.0 g of a mixed enzyme consisting of Protease N, Protease S, and Pancreatin F (all produced by Amano Pharmaceutical Co., Ltd.) at a ratio of 1:1:1 were shaken for four hours at a reaction temperature of 50° C. to effect enzymatic hydrolysis. After the reaction was completed, the reaction mixture was heated at 80° C. for 30 minutes to inactivate the enzyme contained therein. The mixture was centrifuged at 2900 G at 15° C. for 15 minutes and then subjected to suction filtration to expel an insoluble fraction. The liquid fraction obtained consequently was freeze dried to obtain 91.6 g of a protein composition A. The properties of the protein composition A are shown in Table 1.

EXAMPLE 2

A protein composition B, 100.1 g in weight, was obtained by following the procedure of Example 1 except suspending 200 g of the same defatted oil cake as used in Example 1 in 1.6 liters of water and adjusting the suspension to pH 9.0 with 2N sodium hydroxide. The properties of this protein composition B are shown in Table 1.

EXAMPLE 3

A protein composition C, 14.4 g in weight, was obtained by following the procedure of Example 1 except suspending 30 g of the same defatted oil cake as used in Example 1 in 300 ml of a 50 mM phosphate buffer (pH 7.0), adding 1.2 g of a mixed enzyme consisting of Protease S (produced by Amano Pharmaceutical Co., Ltd.) and Alkalase (produced by Novo Nordics) at a ratio of 1:1 to the suspension, and shaking the suspension at a reaction temperature of 50° C. for six hours to effect enzymatic hydrolysis. The properties of the protein composition C are shown in Table 1.

EXAMPLE 4

A protein composition D, 14.1 g in weight, was obtained by following the procedure of Example 1 except suspending 30 g of the same defatted oil cake as used in Example 1 in 300 ml of a 50 mM phosphate buffer (pH 7.0), adding 0.6 g of Protease N (produced by Amano Pharmaceutical Co., Ltd.) to the suspension, and shaking the suspension at a reaction temperature of 55° C. for six hours to effect enzymatic hydrolysis. The properties of the protein composition D are shown in Table 1.

EXAMPLE 5

A protein composition E, 38.6 g in weight, was obtained by following the procedure of Example 1 except suspending 200 g of defatted oil cake produced by hulling sesame seed, grounding the dehulled sesame seed, and defatting the ground sesame seed in 1.6 liters of water, and adjusting the suspension to pH 9.0 with 2N sodium hydroxide. The properties of this protein composition E are shown in Table 1.

EXAMPLE 6

Undehulled sesame seed was defatted by squeezing. The defatted oil cake, 3 g in weight, was suspended in 30 ml of n-hexane. The resultant suspension was filtered to remove n-hexane and expel fat, and the residue was dried in fume hood. The dry residue was suspended in 30 ml of water and adjusted to pH 9.0 with 2N sodium hydroxide. The suspension and 60 mg of a mixed enzyme consisting of Protease N, Protease S, and Pancreatin F (all produced by Amano Pharmaceutical Co., Ltd.) at a ratio of 1:1:1 were together shaken at a reaction temperature of 50° C. for six hours to effect enzymatic hydrolysis. Thereafter, a protein composition F, 0.97 g in weight, was obtained by following the procedure of Example 1. The properties of the protein composition F are shown in Table 1.

EXAMPLE 7

The same defatted oil cake as used in Example 1, 100 g in weight, was suspended in 1.2 liters of water. The resultant suspension was adjusted to pH 10.0 with 2N sodium hydroxide and then shaken at 60° C. for one hour. The suspension was centrifuged at 2900 G at 15° C. for 15 minutes to remove an insoluble fraction. The protein extract, 1 liter in volume, was adjusted to pH 9.0 with 2N sodium hydroxide. This protein extract and 0.5 g of Pancreatin F (produced by Amano Pharmaceutical Co., Ltd.) were together shaken at a reaction temperature of 45° C. for 14 hours to effect enzymatic hydrolysis. Thereafter, a protein composition G, 53.2 g in weight, was obtained by following the procedure of Example 1. The properties of the protein composition G are shown in Table 1.

EXAMPLE 8

The same defatted oil cake as used in Example 1, 50 g in weight, was suspended in 400 ml of 0.5N hydrochloric acid. The suspension was shaken at 90° C. for one hour to effect hydrolysis. After the reaction was completed, the suspension was adjusted to pH 6.5 with 2N sodium hydroxide and centrifuged at 2900 G at 15° C. for 15 minutes to remove an insoluble fraction. The liquid fraction consequently obtained was freeze dried to obtain 22.1 g of a protein composition H. The properties of this protein composition are shown in Table 1.

TABLE 1

| Item | Example 1 Composition A | Example 2 Composition B | Example 3 Composition C | Example 4 Composition D | Example 5 Composition E | Example 6 Composition F | Example 7 Composition G | Example 8 Composition H |
| --- | --- | --- | --- | --- | --- | --- | --- | --- |
| Solubility (%) | 91 | 93.4 | 91.8 | 91.5 | 94.5 | 92.7 | 94.2 | 97.5 |
| Crude protein content (%) | 64.7 | 65.5 | 51.9 | 61.7 | 69 | 46.2 | 55.9 | 54.1 |
| Content of sulfur containing amino acids (%) in amino acid component in crude protein | 4.6 | 4.8 | 4.8 | 4.7 | 5.2 | 4.9 | 5.3 | 5.1 |
| Carbohydrate content (%) | 26.4 | 26.8 | 40.8 | 28.4 | 22.7 | 47.9 | 27.3 | 31.6 |
| Fat content (%) | 0.1 | 0.1 | 0.2 | 0.2 | 0.3 | 0.3 | 2.1 | 0.3 |
| Fiber content (%) | 0 | 0 | 0 | 0 | 0 | 0 | 0.4 | 0 |
| Physiologically active substances content (%) | 0.63 | 0.64 | 0.52 | 0.51 | 1.39 | 0.61 | 2.24 | 0.24 |
| Proportion (%) of W.M. of not more than 5,000 | 25.6 | 29.3 | 15.2 | 9.7 | 8 | 6.6 | 24.2 | 28.7 |
| Proportion (%) of W.M. of not less than 50,000 | 35.8 | 26 | 1.5 | 39.1 | 6.4 | 0.28 | 0 | 0.21 |
| Color tone (powder) | Gray | Gray white | Cream | Cream | Gray white | Brown | Gray | Cream |
| Smell (*) | +++ | + | + | + | + | ++ | ++ | + |

(*) Evalution of smell: The smell was evaluted on a three-point scale, wherein +++ stands for strongly sensed smell and ++ and + stand for gradually weakly sensed smell.

EXAMPLE 9

Sesame protein beverages were manufactured by adding the protein composition G obtained in Example 7 to milk, soybean milk, and a honey-containing soft drink. The amounts of the protein composition G added and the colors and tastes of the sesame protein beverages produced and the presence or absence of occurrence of sediment are shown in Table 2.

TABLE 2

| Item | Milk | | Soybean milk | | Honey-containing soft drink | |
|---|---|---|---|---|---|---|
| Amount added, % | 1 | 3 | 1 | 3 | 1 | 3 |
| Color | White | White | Light cream | Light cream | Light cream | Light cream |
| Taste | No appreciable change | Grew mild | No appreciable change | Smell of soybean milk ceased to exist | No appreciable change | Grew mild |
| Formation of sediment (4° C., four days) | − | − | − | ± | − | − |

−: No sediment formed
±: There was a little sediment formed

The produced sesame protein beverages emitted fine flavor, tasted good, and abounded in nutritive value. Particularly when the protein composition was added in amounts of not more than 5% by weight, the produced beverages tended to produce a mild taste. When the protein composition was added in amounts of 3% by weight, the solubility thereof at 4° C. was invariably fully satisfactory in milk, soybean milk, and honey-containing soft drink.

EXAMPLE 10

The protein composition B obtained in Example 2 was added in an amount of 5% by weight to flour. Cookies and scones were made of this flour. They were visually examined and tested for taste and texture. The results are shown in Table 3.

TABLE 3

| | Cookie | Scone |
|---|---|---|
| Amount added, % | 5 | 5 |
| Appearance | Same as cookies not containing protein composition | Same as scones not containing protein composition |
| Taste | Same as cookies not containing protein composition | Same as scones not containing protein composition |
| Texture | Good texture. More crispy than sample containing no protein composition. | Good texture. More crispy than sample containing no protein composition. |

The produced cookies and scones had fine flavor and good texture, and abounded in nutritive value.

EXAMPLE 11

Cosmetic lotions were prepared by using the protein composition A obtained in Example 1. They were each produced by combining the components 1–8 according to the following formulation, and stirring the resultant mixtures until thorough solution.

| Formulation | |
|---|---|
| 1 Glycerin | 2.00% by weight |
| 2 1,3-Butylene glycol | 6.00% by weight |
| 3 Protein composition A | 2.00% by weight |
| 4 Ethanol | 6.00% by weight |
| 5 Polyethylene glycol (molecular weight 6000) | 0.50% by weight |
| 6 Polyoxyethylene methyl glycoside (10. E.O) | 1.00% by weight |
| 7 Paraoxymethyl benzoate | 0.10% by weight |
| 8 Pure water | 82.40% by weight |

EXAMPLE 12

Shampoos were prepared by using the protein composition G obtained in Example 7. They were each produced by mixing the components 1–8 according to the following formulation, and stirring the resultant mixtures at 70° C.

| Formulation | |
|---|---|
| 1 Laurylsulfuric triethanol amine | 17.00% by weight |
| 2 Coconut Oil fatty acid amide propyl betain | 14.00% by weight |
| 3 Coconut Oil fatty acid diethanol amide | 2.00% by weight |
| 4 Distearic acid ethylene glycol | 2.00% by weight |
| 5 Protein composition G | 3.00% by weight |
| 6 Propylene glycol | 3.00% by weight |
| 7 Methyl paraoxybenzoate | 0.20% by weight |
| 8 Pure water | 58.80% by weight |

EXAMPLE 13

Cosmetic creams were prepared by using the protein composition G obtained in Example 7. Specifically, they were each produced by mixing the components 1–7 shown below by stirring, mixing the resultant mixture with the components 8–11 shown below by stirring, and homogenizing the resultant mixture by stirring and cooling.

| Formulation | |
|---|---|
| 1 Liquid paraffin | 8.00% by weight |
| 2 Cetanol | 0.50% by weight |
| 3 Stearyl alcohol | 2.00% by weight |
| 4 Isopropyl myristate | 2.00% by weight |
| 5 Glycerin monostearate | 0.50% by weight |
| 6 POE(20) cetyl ether | 1.00% by weight |
| 7 Propyl paraben | 0.10% by weight |
| 8 Carbo ball 981 (0.5% aqueous solution) | 20.00% by weight |
| 9 Protein composition G | 2.00% by weight |

-continued

| Formulation | | |
|---|---|---|
| 10 | Methyl paraben | 0.10% by weight |
| 11 | Pure water | 63.80% by weight |

EXAMPLE 14

Functional feeds were obtained by adding the protein compositions A obtained in Example 1 at ratios of 2–5% by weight severally to a feed for beef cattle containing 38.6% by weight of corn, 27.9% by weight of milo, 13% by weight of barley, 9.4% by weight of oily dregs of soybeans (45%), 1% by weight of wheat bran, 2% by weight of alfalfa meal, 5% by weight of honey, 0.5% by weight of table salt, 1.1% by weight of calcium carbonate, 1.3% by weight of tricalcium phosphate, 0.1% by weight of mineral mixture, and 0.1% by weight of vitamin mixture.

According to the present invention, a protein composition which excels in solubility in water and digestive assimilability, contains such physiologically active substances as lignan glycosides and other antioxidant precursors and lignan compounds capable of resisting oxidation which are inherent in sesame seed, and abounds in nutritive value is obtained. Foodstuffs containing this protein composition emits fine flavor and find extensive utility in various applications as nutritive supplements containing physiologically active substances inherent in sesame seed and allowing supply of amino acids in balanced amounts.

Cosmetic articles containing this protein composition have good effect of moisturizing and protecting, and find extensive utility in various applications such as cosmetic lotion, shampoo, cosmetic cream, etc.

What is claimed is:

1. A cosmetic article containing a protein composition derived from sesame seed, wherein said article is selected from the group consisting of cosmetic creams, cosmetic lotions and shampoos, wherein the composition comprises protein, peptides and amino acids extracted from defatted sesame seed oil cake by the method consisting essentially of the steps;
   1) extracting and dissolving the proteins, peptides and amino acids in a non-acidic aqueous medium,
   2) hydrolyzing said solubilized proteins, peptides and amino acids with a combination of enzymes comprising Protease S and Pancreatin F,
   3) separating the soluble proteins, peptides and amino acids from insoluble materials, and
   4) recovering the soluble proteins, peptides and amino acids, wherein the recovered composition contains lignan glycosides.

2. The cosmetic article of claim 1, wherein the combination of enzymes further comprises Protease N.

3. A cosmetic article containing a protein composition derived from defatted sesame seed oil cake wherein said protein composition contains 40–95% by weight of proteins, peptides, and amino acids derived from sesame seed, 1–50% by weight of carbohydrate, 0–1% by weight of fiber, 0–5% by weight of fat, and 0.2–3% by weight of one or more of sesaminol glycosides, sesamin, and sesamolin, lignan glycosides and other antioxidant precursors, and other lignan compounds capable of resisting oxidation, wherein said article is selected from the group consisting of cosmetic creams, cosmetic lotions, and shampoos.

4. The cosmetic article of claim 3 wherein 5–60% of said protein composition derived from sesame seed comprises proteins of molecular weights of not more than 5000 Da, and wherein up to 40% of said proteins have molecular weights of not less than 50,000 Da.

* * * * *